United States Patent [19]

McPherson et al.

[11] Patent Number: 5,573,496

[45] Date of Patent: Nov. 12, 1996

[54] METHOD OF USING A COIL SCREW SURGICAL RETRACTOR

[76] Inventors: William E. McPherson, 14605 Anchoret Rd., Tampa, Fla. 33624; William B. Saye, 4614 Chattahoochee Crossing, Marietta, Ga. 30067; Eddie J. Reddick, 904 Fireside Ct., Brentwood, Tenn. 37027

[21] Appl. No.: 473,447

[22] Filed: Jun. 7, 1995

Related U.S. Application Data

[62] Division of Ser. No. 909,223, Jul. 2, 1992, Pat. No. 5,437,266.

[51] Int. Cl.⁶ .............................. A61B 17/02; A61B 17/5
[52] U.S. Cl. ..................... 600/217; 600/708; 600/209; 600/210; 606/185
[58] Field of Search ........................ 600/204, 208–210, 600/217; 606/222–223, 145, 148, 185

[56] References Cited

U.S. PATENT DOCUMENTS

| | | |
|---|---|---|
| 67,545 | 8/1867 | Hodgins . |
| 196,226 | 10/1877 | Havell . |
| 319,454 | 6/1885 | Cochrane . |
| 343,145 | 6/1886 | Walker . |
| 559,350 | 5/1896 | Bagnall . |
| 843,951 | 2/1907 | Klock . |
| 1,260,924 | 3/1918 | Lossing . |
| 1,592,535 | 7/1926 | Morton . |
| 2,751,912 | 6/1956 | Christoni . |
| 3,857,386 | 12/1974 | Ashbell . |
| 4,024,874 | 5/1977 | Klippel . |
| 4,030,503 | 6/1977 | Clark, III . |
| 4,204,541 | 5/1980 | Kapitanov . |
| 4,745,919 | 5/1988 | Bundy et al. . |
| 4,790,812 | 12/1988 | Hawkins, Jr. et al. . |
| 4,836,190 | 6/1989 | Zwick . |
| 4,883,458 | 11/1989 | Shiber . |
| 4,991,567 | 2/1991 | McCuen, II et al. . |
| 5,195,954 | 3/1993 | Schnepp-Pesch et al. . |
| 5,234,426 | 8/1993 | Rank et al. .................. 606/185 |

*Primary Examiner*—Richard J. Apley
*Assistant Examiner*—Kelly McGlashen

[57] ABSTRACT

A surgical retractor and method for use thereof. The retractor is comprised of an elongate shaft having at one end a screw made of coiled, round wire which terminates at a sharp point for attachment to an organ and a connector at the other end of the shaft. Preferably, the connector comprises an enlarged portion having a polygonal cross section for engagement by a wrench. The retractor is inserted into the peritoneal cavity of a patient through a laparoscopic port and the screw is threaded into the wall of the organ to be retracted, for example, the gallbladder. The organ is resected and thereafter drawn out of the cavity using the retractor.

10 Claims, 4 Drawing Sheets

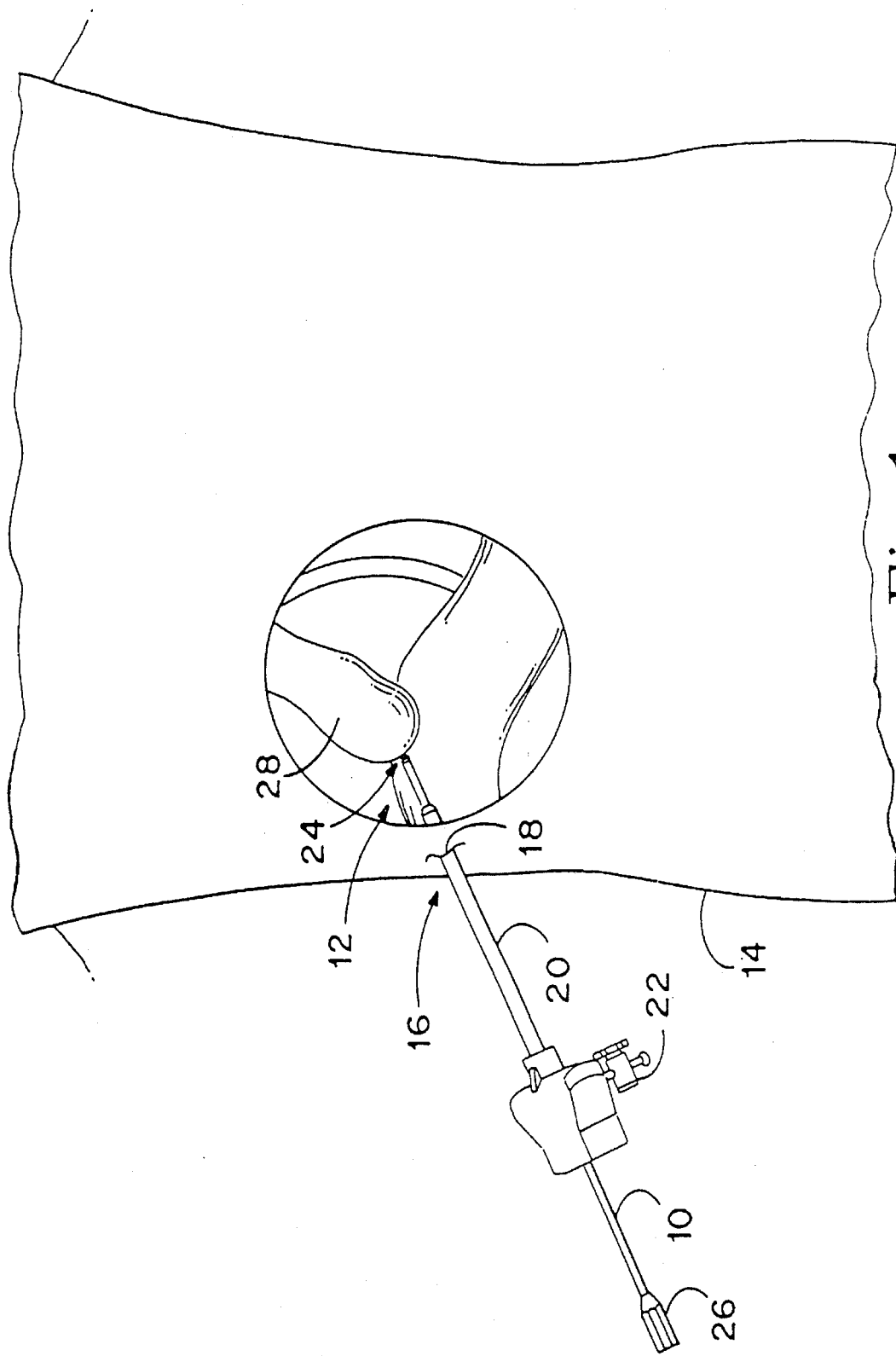

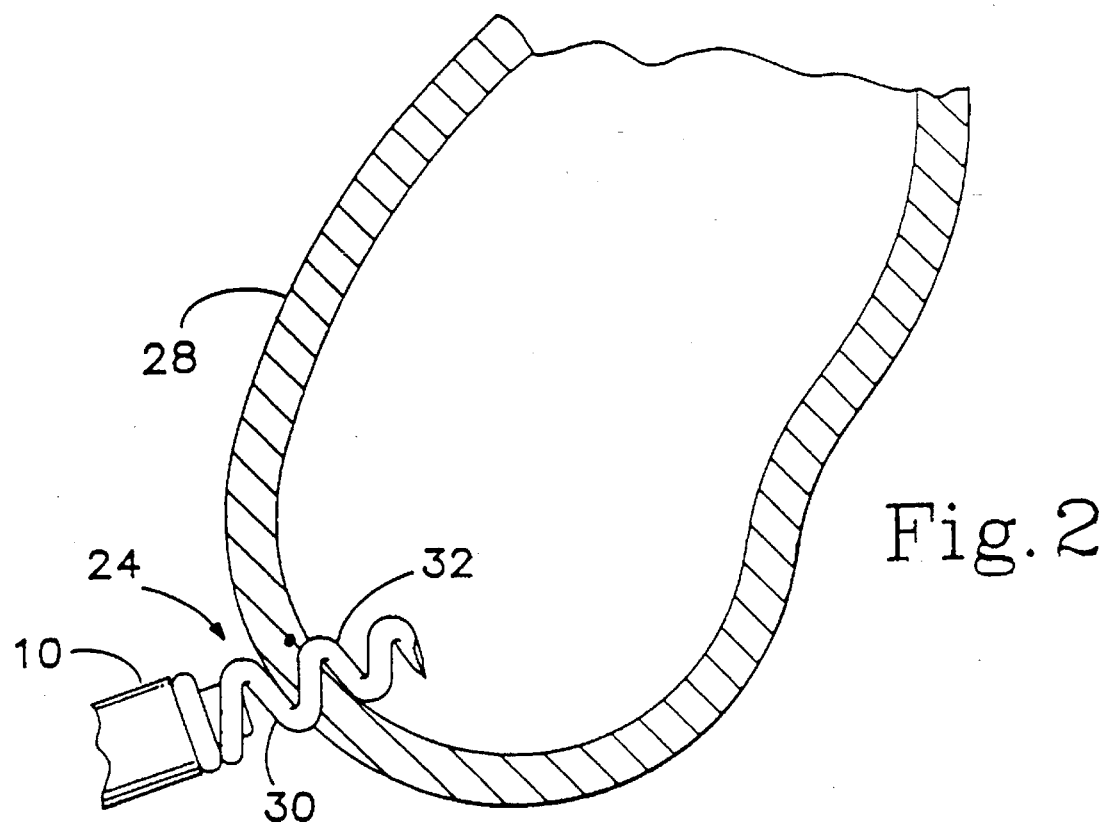

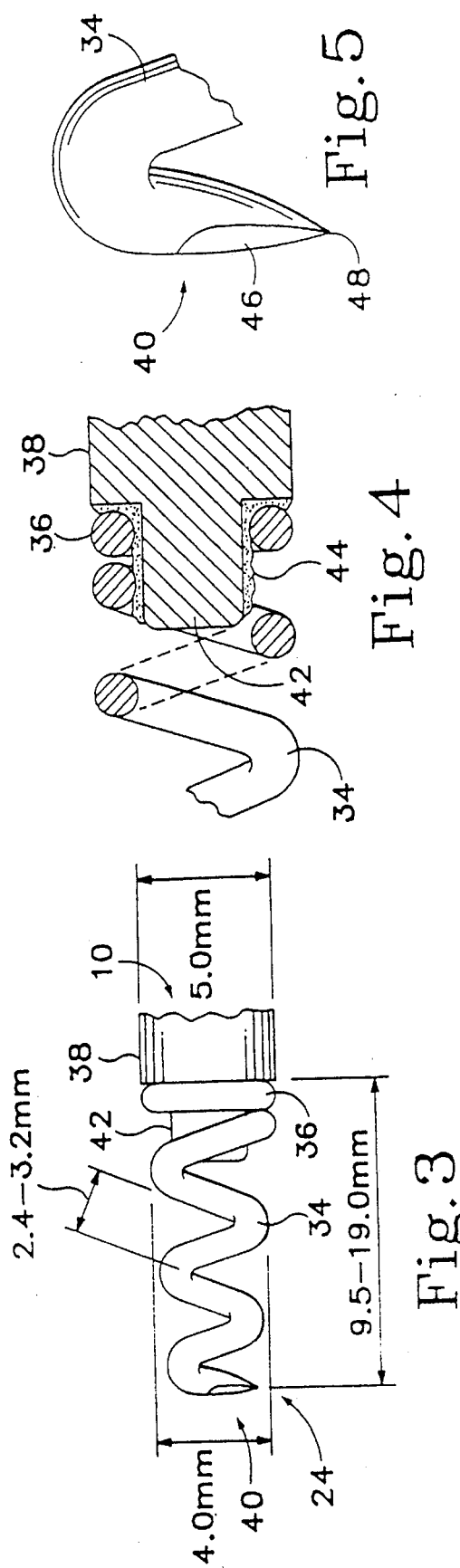
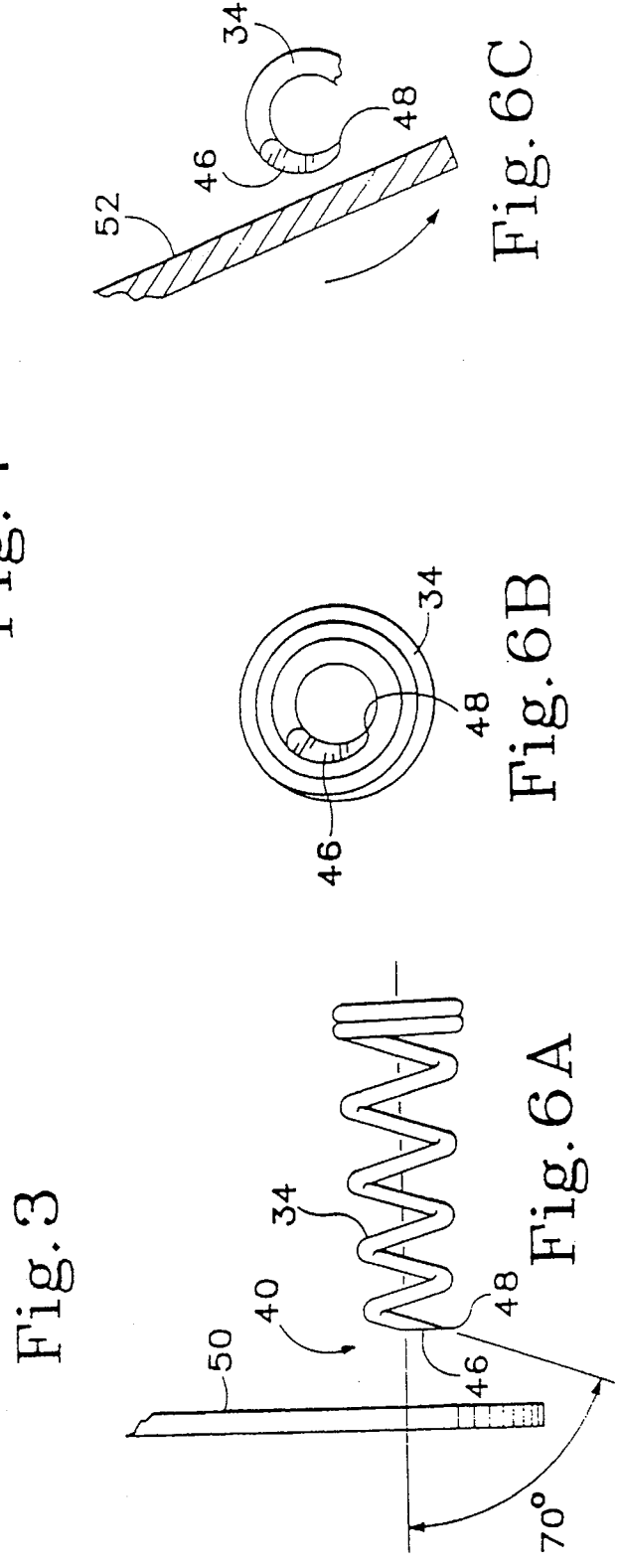

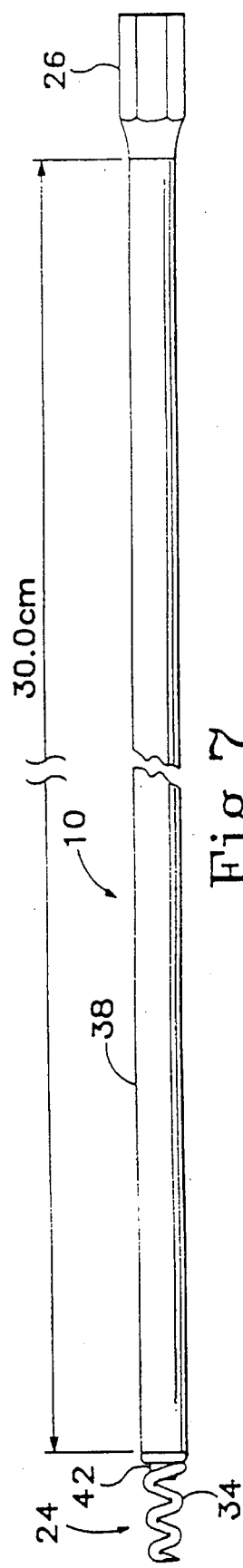
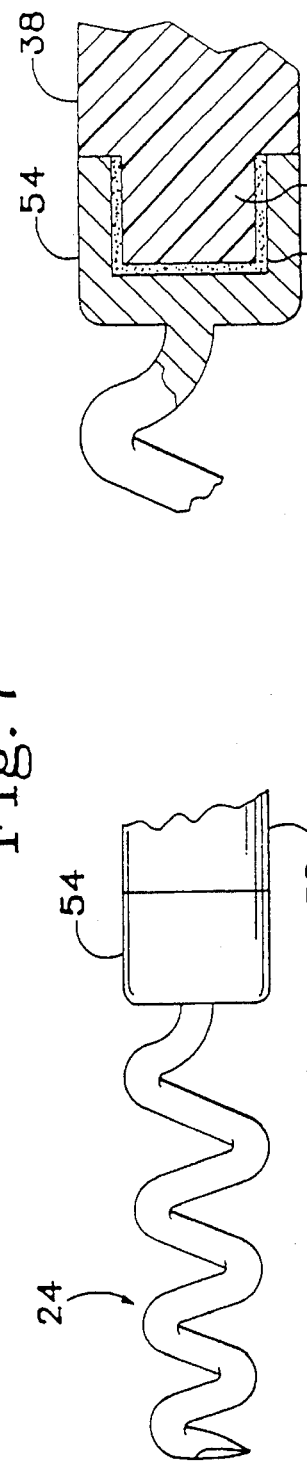
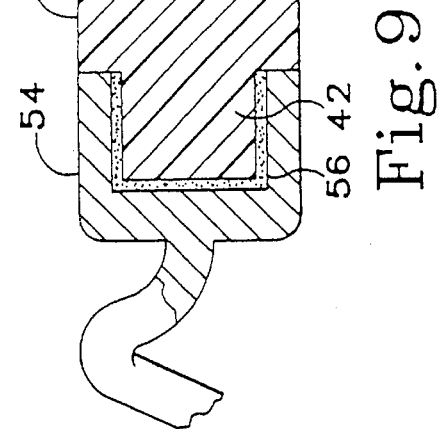
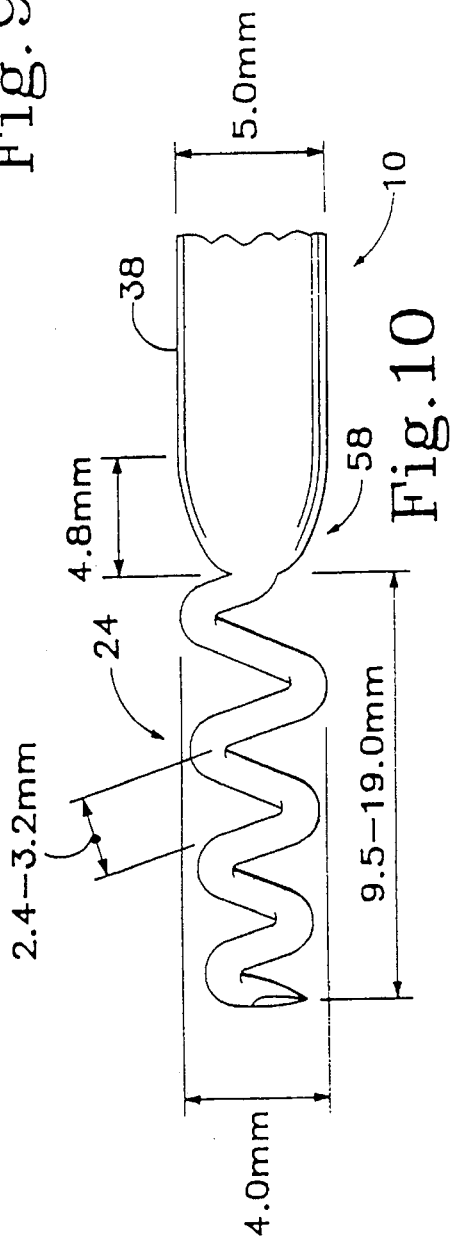

METHOD OF USING A COIL SCREW SURGICAL RETRACTOR

This is a divisional of application Ser. No. 07/909,223, filed on Jul. 2, 1992, now U.S. Pat No.5,437,266.

BACKGROUND OF THE INVENTION

This invention relates to surgical retractors and methods for their use, and particularly to retractors for use in retracting the gallbladder and other organs during laparoscopic procedures, such as laparoscopic cholecystectomy, and methods for their use.

Laparoscopic procedures are often used for performing surgical operations within the abdomen of a patient to minimize the invasion of and trauma to the patient. One such operation is a cholecystectomy, wherein a gallbladder which contains stones or is otherwise diseased is resected. In laparoscopic cholecystectomy the peritoneal cavity is entered just below the umbilicus with an insufflating needle and a pneumoperitoneum is created. At the same site, a port, consisting of a trocar sheath or introducer with a valve to prevent air loss, is introduced into the peritoneal cavity by a trocar. A viewing telescope, typically including a video camera, is inserted through the trocar sheath to inspect the peritoneal cavity. In addition, two lateral ports and one upper midline port are introduced. Typically, the two lateral ports are used for grasping the gallbladder with atraumatic clamps and retracting it to bring its lower end into view. The upper midline port is used for dissection.

In the typical operation, the cystic duct is located, clipped proximally and distally, and divided. The cystic artery is also located, clipped proximally and distally, and divided. The gallbladder is then removed from the gallbladder bed. The telescope is moved to the upper midline port and the gallbladder is grasped using an instrument with a toothed tip inserted through the umbilical port. Then, the gallbladder is drawn into the umbilical trocar sheath and the trocar sheath is drawn out of the peritoneal cavity, pulling the gallbladder out with it.

A significant problem with this procedure is that a diseased or "hot" gallbladder is ordinarily very hard and difficult to grasp with conventional instruments. Clamps tend to slip off the gallbladder, and if adequate pressure is applied to grasp the gallbladder, the clamps tend to puncture it. In the former case, the completion of the operation is hampered and in the latter case, infection may result. A similar problem occurs in the retraction of other organs, such as a diseased ovary, during other laparoscopic procedures.

Accordingly, there is a need for an improved retractor and method for use thereof in laparoscopic procedures.

SUMMARY OF THE INVENTION

The present invention overcomes the aforementioned problems with prior art devices used to retract gallbladders during laparoscopic procedures, and meets the aforementioned need for an improved retractor and procedure, by providing a retractor that is inserted into the gallbladder or other organ and fastened securely to the wall of the organ. Preferably, the retractor comprises an elongate member, or shaft, having an attachment element at one end for securely fastening the retractor to the gallbladder, and a connector at the other end for connecting a tool to manipulate the retractor. Preferably, the attachment element comprises a screw made of coiled, round wire which is attached at one end to the shaft and terminates at the other end in a sharp point. Preferably, the connector at the other end of the shaft comprises an enlarged portion having a polygonal cross section which can easily be engaged by a wrench. The shaft is preferably made of a substantially rigid material suitable for surgical operation, such as stainless steel. The screw may be attached to the shaft by solder, by a weld, by an adhesive or simply by forming the end of the shaft into a screw.

In use, the retractor is inserted into the peritoneal cavity through one of the laparoscopic ports and threaded into the wall of the organ to be retracted, for example, the gallbladder. The loops of the screw should be of a spacing such that when the screw is threaded into the wall of the organ, one loop lies on one side of the wall and another loop lies on the other side of the wall, thereby allowing the organ to be manipulated by either a pushing or a pulling motion. The retractor may be more readily manipulated by attachment of a wrench or other tool to the connector portion of the shaft. Once the organ is firmly attached to the retractor by the screw, the organ may then be resected. In the case of the gallbladder, it is held firmly by the retractor while being separated from its bed and drawn into the trocar sheath by pulling back on the retractor. Thereafter, it is pulled out of the peritoneal cavity by the retractor, along with the trocar sheath.

Accordingly, it is a principal object of the present invention to provide a novel and improved surgical retractor and method for use thereof.

It is another principal object of the present invention to provide a novel and improved surgical retractor for use in laparoscopic surgical procedures.

It is yet another object of the present invention to provide a novel and improved retractor and method for use thereof in laparoscopic cholecystectomy.

The foregoing and other objects, features, and advantages of the invention will be more readily understood upon consideration of the following detailed description of the invention, taken in conjunction with the accompanying drawings.

BRIEF DESCRIPTION OF THE DRAWINGS

FIG. 1 is a partially cut away view of the abdomen of a patient showing a laparoscopic port, a trocar sheath inserted therein and a preferred embodiment of a retractor according to the present invention inserted through the port and attached to the gallbladder of the patient.

FIG. 2 shows a partial cross section of a gallbladder having a retractor according to the present invention inserted therein.

FIG. 3 is a side view of a coil screw of a preferred embodiment of a retractor according to the present invention, with a portion of the retractor cut away.

FIG. 4 is a side section of the coil screw of FIG. 3.

FIG. 5 is a detail view of the point of a coil screw of a preferred embodiment of a retractor according to the present invention.

FIG. 6A is a side view of a coil screw of a retractor according to the present invention together with a grinding wheel for forming the tip thereof.

FIG. 6B is a front end view of a coil screw of a retractor according to the present invention.

FIG. 6C is a front end view of a coil screw of a retractor according to the present invention together with a file for forming the tip thereof.

FIG. 7 is a side view of a preferred embodiment of a retractor according to the present invention.

FIG. 8 is a side view of a coil screw of a first alternative embodiment of a retractor according to the present invention, with a portion of the retractor cut away.

FIG. 9 is a side section of the coil screw of Figure 8.

FIG. 10 is a side view of a coil screw of a second alternative embodiment of a retractor according to the present invention.

DETAILED DESCRIPTION OF THE INVENTION

In FIG. 1, a preferred embodiment 10 of a retractor according to the present invention is shown inserted into the peritoneal cavity 12 of a patient 14 through laparoscopic port 16. The laparoscopic port is formed by inserting a trocar through an incision 18 in the abdomen so as to place a trocar sheath or introducer 20 therethrough. The retractor is longer than the sheath. The trocar and trocar sheath or introducer may be any of several commercially available types of suitable sizes for receiving the retractor, but should preferably include a valve 22 for inflating the peritoneal cavity and holding air therein.

The retractor 10 has a coil screw 24 disposed at the distal end thereof and the connector 26 disposed at the proximal end thereof. The retractor is attached to the gallbladder 28 by the coil screw 24 for manipulation of the gallbladder.

Turning to FIG. 2, which shows a cross section of a portion of the gallbladder 28 and the distal end of the retractor 10, it can be seen that the loops of the coil screw are spaced so that when the coil screw is threaded into the gallbladder one loop, e.g., loop 30, rests on one side of the gallbladder wall and another loop, e.g., loop 32, rests on the other side of the gallbladder wall. This ensures that the coil screw will not slip out of the gallbladder, or be pushed into the gallbladder, by longitudinal force on the retractor. Since the wall of a hot gallbladder is typically about 2.4–3.2millimeters in thickness, the spacing of the loops of the coil should preferably be about 2.4–3.2millimeters, as shown in FIG. 3. Also, it has been found that a tapered coil screw having a maximum diameter of about 4 millimeters works best and that the screw should be about 9.5–19.0millimeters in length to allow adequate attachment to the gallbladder while avoiding puncture of the wall of the gallbladder opposite the entrance of the coil screw.

Preferably, the coil screw 24 is formed of a round wire 34 wrapped in the form of a coil with a circular loop 36 at one end for attachment to a shaft 38 of the retractor and a sharp point 40 at the other end. The shaft 38 includes a reduced portion 42 for receiving the circular loop 36. The circular loop is preferably glued to the end of the shaft by an adhesive 44, as shown in FIG. 4, but could also be attached by welding or brazing. Preferably, the round wire is made of stainless steel about 0.029inches in diameter, though it is to be recognized that other materials and other sizes may be used depending upon the circumstances, without departing from the principles of the invention. The point 40 is shown in greater detail in FIG. 5 wherein it can be seen that it has a flat front surface 46 resulting in a sharp tip 48.

Preparation of the point 40 is shown in FIGS. 6A, 6B and 6C. Once formed into a coil, the wire 34 is ground at its point by a grinding wheel 50 to form the flat surface 46, resulting in a sharp tip 48. The edges of the flat surface are then filed using a file 52, or other appropriate tool, to obtain a sharp point. The axis of the wire 34 preferably forms an angle of about 70–110 degrees with the axis of the shaft, the flat surface 46 being substantially perpendicular to the axis of the shaft.

The entire preferred embodiment of the retractor 10 is shown in FIG. 7. As can be seen, it is essentially an elongate shaft 38 having the connector 26 at the proximal end and the coil screw 24 at the distal end. The outside diameter of the shaft should preferably be only slightly less than the inside diameter of the trocar sheath 20 so as to minimize the space therebetween. A typical diameter for the shaft would be about 5millimeters. The coil screw 24 should preferably have an outside diameter no greater than the maximum outside diameter of the shaft, so that it will fit through the trocar sheath while permitting a close fit between the sheath and the shaft. The shaft is preferably made of stainless steel, though other materials suitable for introduction into the body during a surgical operation may also be used. Preferably, the shaft should be about 30 centimeters in length.

A first alternative embodiment of the retractor is shown in FIGS. 8 and 9. In that embodiment the coil screw 24 is formed with a cap 54 placed over the reduced portion 42 of the shaft 38 and fastened by an adhesive 56.

Yet a further embodiment of the retractor is shown in FIG. 10. In this case the coil screw 24 is formed simply as an extension of the shaft 38. That is, the shaft 38 has a tapered portion 58, preferably about 4.8 millimeters in length, which turns into the coil screw 24. Preferably, the entire part is made of stainless steel.

In use, the retractor 10 is inserted into the peritoneal cavity 12 through the trocar sheath 20 and threaded into the gallbladder 28 to manipulate the gallbladder. Preferably, the gallbladder is first aspirated with a needle introduced through another trocar sheath. Using the retractor, the gallbladder is positioned for clamping and dividing the cystic duct and the cystic artery. It is also manipulated to remove the gallbladder from its bed. The gallbladder is then drawn into the trocar sheath by pulling outwardly on the retractor and removed through the incision in the abdomen along with the trocar sheath itself. The connector 26 may be grasped by a wrench for rotation, as well as lateral manipulation and pushing and pulling of the retractor, to perform these procedures.

The terms and expressions which have been employed in the foregoing specification are used therein as terms of description and not of limitation, and there is no intention in the use of such term and expressions of excluding equivalents of the features shown and described or portions thereof, it being recognized that the scope of the invention is defined and limited only by the claims which follow.

We claim:

1. A method for using a surgical retractor assembly to retract an organ in the body of an animal, said method comprising:

(a) providing a retractor assembly comprising an elongate tubular sheath, and a shaft having a proximal end and a distal end, and a coil screw attached to said distal end of said shaft, said coil screw comprising an elongate wire wound into a coil and terminating with a substantially flat outer surface at said tip, a sharp edge being formed on said coil member at said tip by the intersection of said flat surface and the round surface of said wire;

(b) inserting said sheath into the body of an animal;

(c) introducing said shaft into said body of said animal by inserting it through said sheath, distal end first;

(d) positioning said coil screw adjacent said organ;

(e) rotating said retractor so as to screw said coil screw into said organ; and (f) manipulating said organ by moving said retractor after it has been screwed into said organ.

2. The method of claim 1, wherein said organ comprises a gallbladder, said method further comprising aspirating said gallbladder prior to screwing said retractor into said gallbladder.

3. The method of claim 1, wherein said organ comprises a gallbladder, and said method is part of a laparoscopic cholecystectomy procedure.

4. The method of claim 1, wherein said organ is a gallbladder and the spacing between loops of said coil screw is substantially about 2.4 to 3.2 millimeters.

5. The method of claim 1, wherein said organ is a gallbladder and the spacing between loops of said coil screw is selected to be in a range on the order of the range of thicknesses of the wall of said gallbladder.

6. The method of claim 1, wherein said organ is a gallbladder and the spacing between loops of said coil screw is selected to be less than the range of thicknesses of the wall of said gallbladder.

7. The method of claim 1, wherein said organ is a gallbladder and the spacing between loops of said coil screw is substantially about 1.0 to 2.4 millimeters.

8. The method of claim 1, wherein the loops of said coil screw form an angle with the axis of said shaft of substantially about 70 to 110 degrees.

9. The method of claim 1, wherein said coil screw comprises an elongate wire wound into a coil and said wire has a predetermined cross-sectional shape and size so as to enhance insertion of the retractor into said organ by screwing and to optimize manipulation of said organ thereafter.

10. The method of claim 1, wherein said coil screw has a longitudinal central axis and a tip terminating in a pointed cutting edge disposed substantially laterally from and perpendicular to said central axis, so as to be substantially blunt and thereby minimize trauma to the organ when the tip is brought in contact with the organ by movement of the retractor in the direction of said central axis.

* * * * *